United States Patent [19]
Hajjar

[11] Patent Number: 6,126,653
[45] Date of Patent: *Oct. 3, 2000

[54] LASER THERAPY SYSTEM AND METHOD OF CUTTING AND VAPORIZING A TISSUE BODY

[76] Inventor: John H. Hajjar, 90 Hoover Dr., Cresskill, N.J. 07626

[*] Notice: This patent is subject to a terminal disclaimer.

[21] Appl. No.: 08/455,816

[22] Filed: May 31, 1995

Related U.S. Application Data

[62] Division of application No. 08/254,023, Jun. 3, 1994, Pat. No. 5,456,681.

[51] Int. Cl.[7] .................................................. A61B 17/36
[52] U.S. Cl. ............................................... 606/15; 606/16
[58] Field of Search .................................. 606/14, 15, 16, 606/17, 10, 11, 12

[56] References Cited

U.S. PATENT DOCUMENTS 5,320,617  6/1994  Leach ........................................ 606/15
5,456,681  10/1995  Hajjar ........................................ 606/15

Primary Examiner—John P. Leubecker
Assistant Examiner—Sonja Harris-Ogugua
Attorney, Agent, or Firm—Kile McIntyre Harbin & Lee

[57] ABSTRACT

A laser therapy system and method of cutting and vaporizing a tissue body which includes a fiber optic which is inserted into the lumen of a catheter and operable between an extended position wherein a distal end portion of the fiber optic is positioned to cut and vaporize a tissue body and a retracted position wherein the fiber optic is received within the lumen of the catheter. The catheter incorporates at a distal end portion a means for removing attached tissue fragments and the like from the distal end portion of the fiber optic such that tissue fragments stuck to the distal end portion of the fiber optic can be removed while the catheter and fiber remain at the treatment site. This improved system eliminates the need to completely remove the fiber optic during the cutting and vaporization procedure in order to remove the fragments and debris.

4 Claims, 3 Drawing Sheets

LASER THERAPY SYSTEM AND METHOD OF CUTTING AND VAPORIZING A TISSUE BODY

This application is a division of application Ser. No. 08/254,023, filed Jun. 3, 1994, now U.S. Pat. No. 5,456,681.

BACKGROUND OF THE INVENTION

The present invention relates to a laser therapy system and method for cutting and vaporizing a tissue body. More specifically, the invention is directed to an improved system and method for cutting and vaporizing a tissue body utilizing a fiber optic which is inserted into the lumen of a catheter and operable between an extended position wherein a distal end portion of the fiber optic is positioned to cut and vaporize a tissue body and a retracted position wherein the fiber optic is received within the lumen of the catheter. The catheter incorporates at a distal end portion a means for removing attached tissue fragments and the like from the distal end portion of the fiber optic.

Laser therapy techniques have been utilized in a variety of surgical procedures in a variety of specialties for a number of years. For example, laser techniques find applications in urology, gynecology, general surgery, ENT and other surgical specialties. Generally in laser techniques, a fiber optic is inserted into a working channel of a cystoscope and directed to a treatment sight where a tissue body is located. At the treatment sight the tissue body is then photoirradiated with a sufficient quantity of energy to cut, vaporize, and coagulate the tissue body.

Laser therapy has been a preferable alternative to conventional surgical procedures for a number of reasons. First, a surgical procedure can be performed with local disease control with functional and cosmetic results superior to standard techniques. Second, a surgical procedure can be performed with a drastic reduction in patient trauma and morbidity. Third, the overall surgical procedure time is reduced with the use of laser therapy as opposed to conventional techniques.

More recently, laser technology has been useful in the management of bladder-outlet obstruction due to prostatic hyperplasia (i.e. prostate swelling). Prostatic hyperplasia has been traditionally treated with a technique known as transurethral rejection of the prostate (TURP). This procedure utilizes an electrocautery loop which cuts, for example, a urethral obstruction into pieces thereby freeing the bladder passage. Although this technique has proven successful and represents a major advance over open surgical prostatic enucleation, there still remains a significant post-operative morbidity and patient trauma associated with this procedure. Laser therapy is used to supplement the TURP treatment and in some cases completely replace the need for TURP.

One of the problems associated with laser therapy has been the difficulty of directing the laser energy from the distal end of the fiber optic to the tissue body. This is because the surgeon would have difficulties viewing the procedure when fragments and debris engulfed the distal portion of the fiber and blocked viewing through a conventional cystoscope. In order to alleviate this problem LASERSCOPE® SURGICAL SYSTEMS developed an improved fiber system incorporating an Angled Delivery Device (ADD)™ which directed the laser energy from the fiber axis as opposed to the distal end of the fiber. This allowed for improved viewing by the surgeon because the viewing light would not be detracted through the fragments and debris when viewed through a cystoscope. The ADD™ consist of a metal cannula having a fiber optic inserted therein which is manufactured to deflect at the distal end portion laser energy approximately 70 degrees off the central axis of the fiber. The metal cannula has an opening at a distal end portion which is filled with a glass thereby creating a window through which laser energy from the fiber is projected. With the development of the ADD™, however, it became critical to remove the fragments and debris which became stuck on the side of the distal end of the ADD™ during the vaporization procedure. If the fragments and debris are not removed, the laser energy is not permitted to effectively cut and vaporize remaining tissue body. Moreover, if the fragments are allowed to remain on the outer surface of the ADD™, an insulation effect is generated and a large heat build up will occur which melts the glass window and degrades the fiber. More recently, LASERSCOPE™ SURGICAL SYSTEMS has developed an ADD™ STAT which is utilized in a number of surgical procedures including the management of prostate swelling. This system comprises a fiber optic with an outer plastic sheath and a glass end cap secured on the distal end portion of the sheath. The ADD™ STAT does not utilize a metal cannula as with the ADD™. When using the ADD™ STAT fragments and debris will become attached to the glass cap which must be removed for the same reasons described above. In this, the surgeon is required to remove the fiber system from the cystoscope and wipe the window or cap free of tissue fragments and debris which drastically extends procedure time and patient trauma.

As noted above, fragment and debris removal is more critical when the ADD™ or ADD™ STAT is used as opposed to distal end emitting fibers. However, such fragment and debris build up on the fiber system is disadvantageous in all laser therapy procedures whether the laser energy is side or end directed.

The difficulties and limitations suggested in the preceding are not intended to be exhaustive, but rather are among many which demonstrate that although significant attention has been devoted to laser therapy systems and techniques, the laser therapy systems and techniques appearing in the past will admit to worthwhile improvement.

OBJECTS AND BRIEF SUMMARY OF THE INVENTION

It is therefore a general object of the invention to provide a novel laser therapy system and method of cutting and vaporizing a tissue body which will obviate or minimize difficulties of the type previously described.

It is a specific object of the invention to provide a laser therapy system and method of cutting and vaporizing a tissue body which will reduce patient trauma and morbidity.

It is another object of the invention to provide a laser therapy system and method of cutting and vaporizing a tissue body which will optimize surgical working conditions.

It is still another object of the invention to provide a laser therapy system and method of cutting and vaporizing a tissue body which will allow the use of standard cystoscope and radiation equipment.

It is yet another object of the invention to provide a laser therapy system and method of cutting and vaporizing a tissue body which will allow for and insure only localized cutting and vaporization at a treatment site.

It is still yet another object of the invention to provide a laser therapy system and method of cutting and vaporizing a tissue body which may be easily used and performed by a surgeon of any skill.

It is still another object of the invention to provide a laser therapy system and method of cutting and vaporizing a tissue body which may be used in a variety of surgical procedures including but not limited to urology, gynecology, general surgery, ENT and other surgical specialties.

BRIEF SUMMARY OF A PREFERRED EMBODIMENT OF THE INVENTION

A preferred embodiment of the invention which is intended to accomplish the foregoing objects includes a fiber optic which is inserted into the lumen of a catheter and operable between an extended position wherein a distal end portion of the fiber optic is positioned to cut and vaporize a tissue body and a retracted position wherein the fiber optic is received within the lumen of the catheter. The catheter incorporates at a distal end portion a means for removing attached tissue fragments and the like from the distal end portion of the fiber optic such that tissue fragments stuck to the distal end portion of the fiber optic can be removed while the catheter and fiber remain at the treatment site. This improved system eliminates the need to completely remove the fiber optic during the cutting and vaporization procedure in order to remove the fragments and debris.

DRAWINGS

Other objects and advantages of the present invention will become apparent from the following detailed description of a preferred embodiment thereof taken in conjunction with the accompanying drawings, wherein.

DETAILED DESCRIPTION

Figure 1:
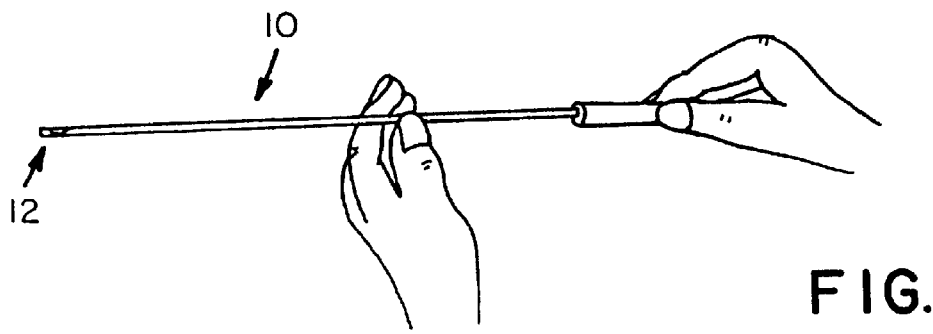
FIG. 1 is a pictorial view showing an Angled Delivery Device as manufactured by LASERSCOPE® SURGICAL SYSTEMS.
Figure 2:
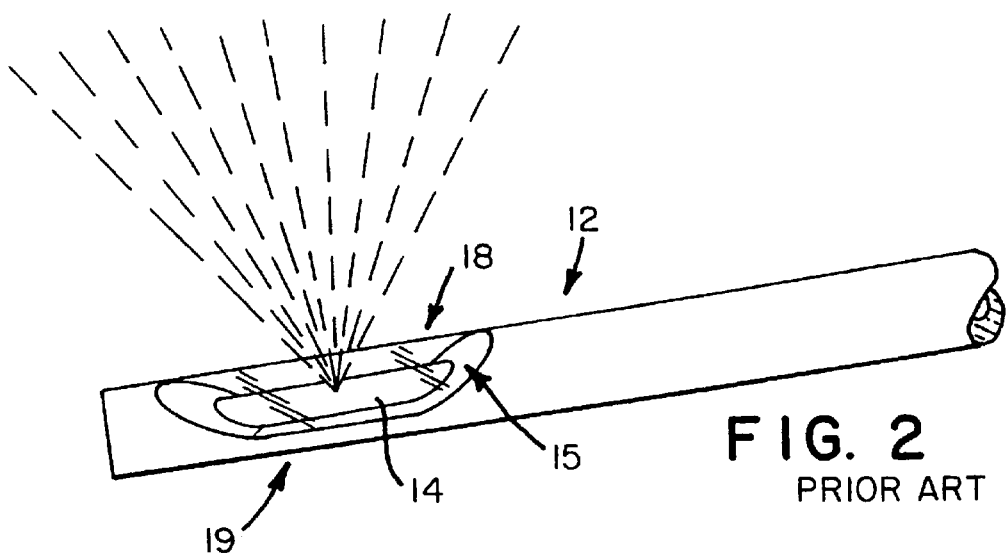
FIG. 2 is a pictorial view showing an end portion of the Angled Delivery Device as manufactured by LASERSCOPE® SURGICAL SYSTEMS.

Referring now to the drawings and particularly to FIG. 1, there is shown an ADD™ 10 as manufactured by LASERSCOPE® SURGICAL SYSTEMS. In FIG. 2 there is shown the end portion 12 of the ADD™ 10. The ADD™ shown in FIGS. 1 and 2 does not form a part of the present invention per se. The side directed energy beam is oriented at an angle of approximately 70 degrees to the fiber 14 axis. The fiber 14 is manufactured in a manner so as to deflect the laser energy off the fiber axis. A metal cannula 16 encloses the fiber except at an end portion where an opening 18 in the cannula allows the laser energy to escape. The opening 18 in the cannula is filled with a glass 15 which isolates the fiber 14 from the surroundings. The metal cannula 16 has a diameter of approximately 1 mm and the fiber 14 has a diameter of approximately 400 microns or 0.4 mm. In standard operation the ADD™ is placed in a receiving channel of a cystoscope and delivered to a treatment site, for example, to a bladder and adjacent a prostate. At the treatment site, the energy is delivered through the fiber 14 using a standard energy device such as a neodymium:YAG (Nd:YAG). The supplied laser energy will cut and vaporize the body tissue. The energy level delivered will vary depending upon the surgical procedure. When utilizing the ADD™ the energy level usually ranges from 85 watts of 1064 nm laser energy and up to 34 watts of 532 nm laser energy in a fluid environment with continuous irrigation flowing through the cannula of the cystoscope. As noted above, during the cutting and vaporization process tissue fragments and debris become stuck on the window glass 15. The attached tissue fragments and debris degrade the performance of the ADD™ and interfere with the beam delivery. Moreover, if the fragments are allowed to remain on the window glass 15, a critical heat build up will occur and cause the glass to break down and destroy the fiber 14. As such, it is critical that the fragments are removed before further cutting and vaporization of the tissue body. Presently, this is accomplished by removing the ADD™ out of the cystoscope, cleaning the window 15 of the ADD™ 10, and reinserting the ADD™ back into the receiving channel of the cystoscope and to the treatment site. This additional procedural step increases the overall surgical procedure time and patient trauma.

Figure 3:
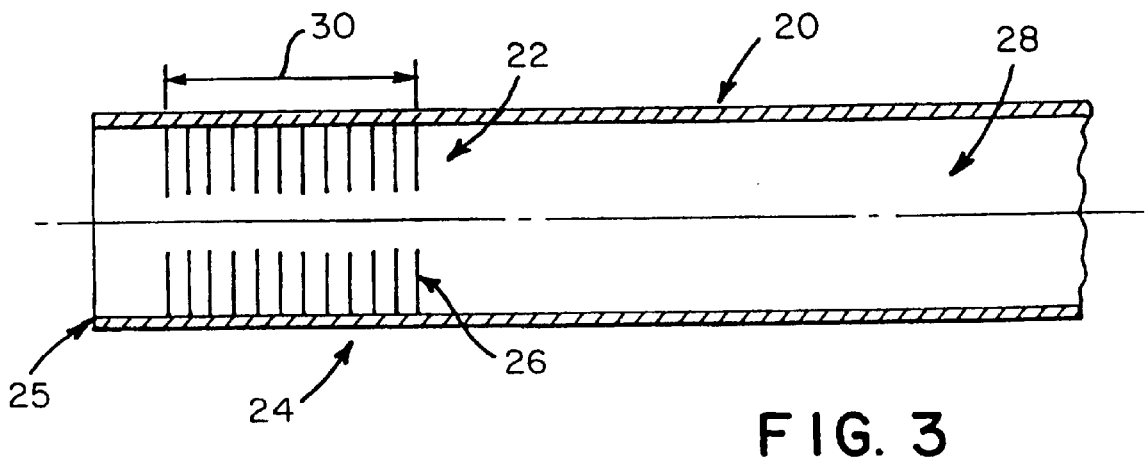
FIG. 3 is a side view showing a catheter incorporating a brush at its distal end in accordance with the present invention.

The laser therapy system of the present invention is designed to eliminate the need of withdrawing the fiber during the surgical procedure. Shown in FIG. 3 is a preferred embodiment of the present invention. A catheter 20 incorporates a brush assembly 22 secured at a distal end portion 24 of the catheter 20. The catheter can be of any longitudinal length depending on the type of surgical procedure and laser equipment utilized. For example, a length of approximately 50 cm is generally acceptable. The catheter 20 is preferably constructed of a soft and flexible material which will permit bending of the catheter during the delivery process. For example, a catheter constructed from polytetraflouroethylene provides adequate flexibility. The catheter may have a diameter of any suitable dimension depending on the particular surgical procedure. A catheter diameter of 8–12 F. is suitable for most procedures such as those relating to urology. The brush elements 26 may be secured to the catheter either individually or as a brush unit. Individual attachment may be achieved, for example, by threading the elements through the wall of the catheter 20, gluing the elements to the side wall of the catheter, or utilizing a double wall at the distal end portion 24 of the catheter with the ends of the elements 26 through the first wall and secured by the second wall. All suitable securing techniques are considered to be within the scope of the invention. If the brush elements are secured as a unit, the brush elements are secured to a separate cylindrical body (not shown) or the like which in turn is placed and secured in the lumen 28 of the catheter 20. The preferred manner of attachment will vary depending on the particular use of the catheter and required working dimensions. The brush assembly longitudinally extends a distance 30 along the catheter 20. The preferred distance will depend on the particular use of the catheter and the type of fiber elements used. The preferred distance 30 is approximately 2.5 cm when using the catheter 20 with the ADD™ 10 in a prostate cutting and vaporization procedure.

Figure 4A:
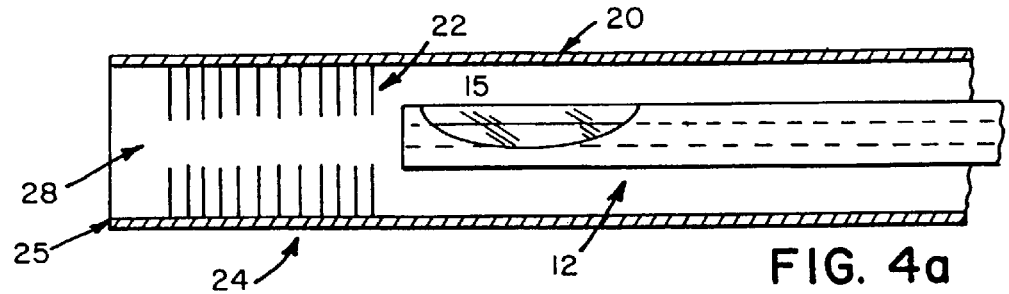
FIGS. 4a through 4e shows a side view of the catheter incorporating a brush at its distal end in cooperation with an Angle Delivery Device and a method of using the laser therapy system in accordance with the present invention.
Figure 4B:
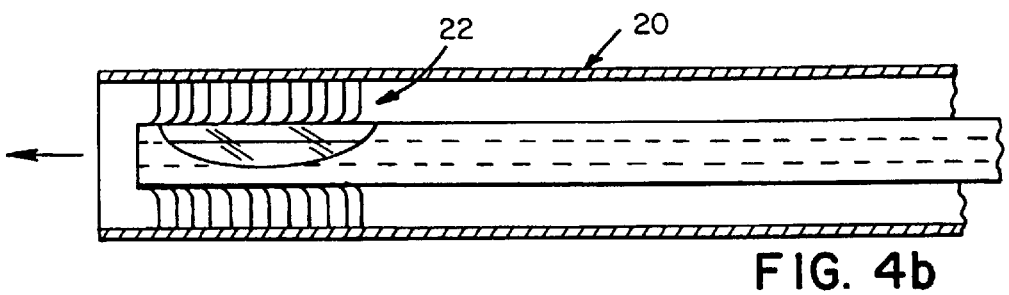
Figure 4C:
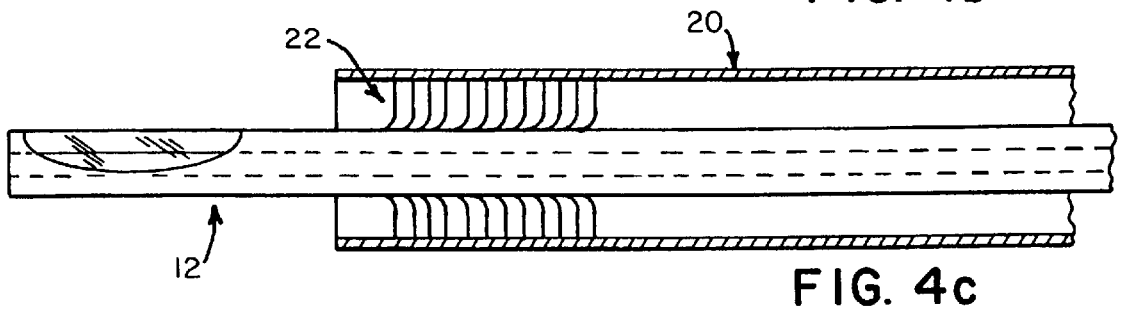
Figure 4D:
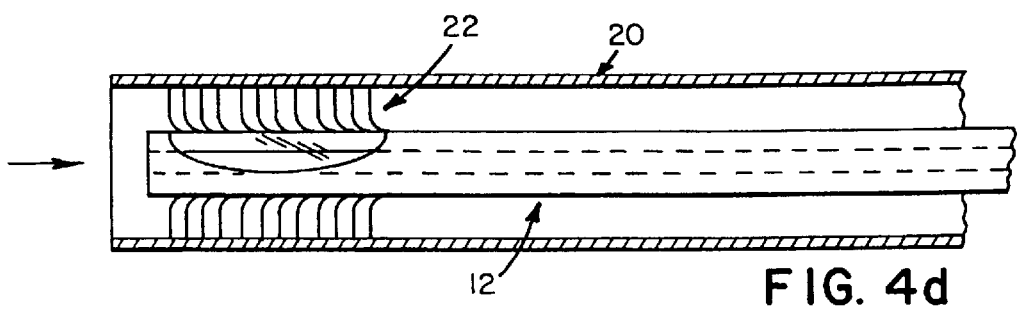
Figure 4E:
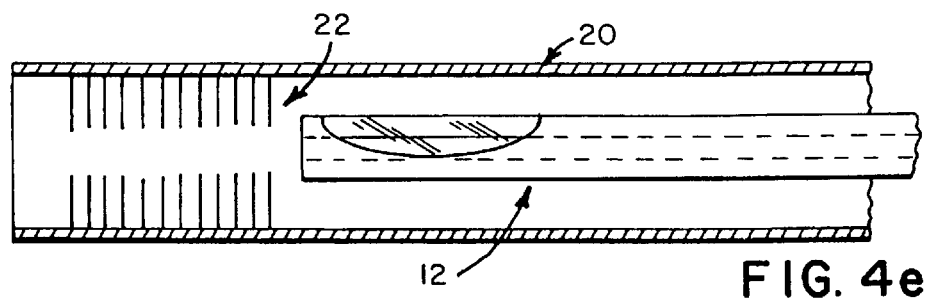

In FIGS. 4a through 4e there is shown the catheter 20 in cooperation with an Angle Delivery Device 10 and a method of using the laser therapy system in accordance with the present invention. In FIG. 4a, the ADD™ 10 is received within the lumen 28 of the catheter 20. Although the drawings depict using the catheter of the present invention with an ADD™, it is to be understood that the use of any fiber system is considered within the scope of the invention. After the ADD™ 10 is inserted into the lumen of the catheter 20, the catheter 20 with the received ADD™ 10 is inserted into the receiving channel of a cystoscope. Of course, in a procedure where a cystoscope is not required, then the catheter 20 with ADD™ is directed to the treatment site without the assistance of a cystoscope. Once the catheter 20 is properly positioned at a treatment site, for example a bladder and adjacent to a prostate, the ADD™ 10 or the particular fiber that has been inserted, is moved forward toward the distal end 25 of the catheter 20. As the distal end portion 19 of the ADD™ 10 is moved toward the distal end 25 of the catheter 20, the end portion 19 travels through the brush assembly 22. FIG. 4c shows the ADD™ in an extended position. The extension distance required will vary depending upon the surgical procedure and the position of the catheter at the treatment site. In this extended position, laser energy is supplied through the fiber 14 and is directed out the side opening 18 and through window 15. The surgeon will continue to laze the tissue body until a certain quantity of tissue fragment and debris become stuck on the window 15. At this time, cutting and vaporization of the tissue body is severely hindered by the presence of the fragments and continued use with the fragments attached will degrade glass 15 and destroy the fiber 14. At this time, the surgeon will retract the ADD™ in the direction shown in FIG. 4d. As the distal end 19 of the ADD™ 10 is retracted into the catheter 20, the brush elements 26 wipe the window 15 and remove at least some of the attached fragments. If tissue fragments still remain on the window 15 after a first pass through the brush assembly 22, then additional passes may be necessary. This is accomplished by simply extending the ADD™ in the direction shown in FIG. 4b and repeating the movements shown in FIGS. 4c through 4e until the window 15 is sufficiently free of fragments and debris. The surgeon may then proceed with the cutting and vaporization procedure and if necessary, repeat the brushing process.

As noted above, the Figures depict using the catheter with brush assembly of the present invention with an ADD™ as manufactured by LASERSCOPE® SURGICAL SYSTEMS, however, the scope of the invention includes any type of fiber optic used in laser therapy. For example, ADD™ STAT manufactured by LASERSCOPE® SURGICAL SYSTEMS is a preferable fiber optic utilized in prostate treatments. This system comprises a fiber optic with an outer plastic sheath and a glass end cap secured on the distal end portion of the sheath. The ADD™ STAT does not utilize a metal cannula as with the ADD™ shown in the figures. When using the ADD™ STAT fragments and debris will become attached to the glass cap which are removed utilizing the brush assembly as described above.

Figure 5A:
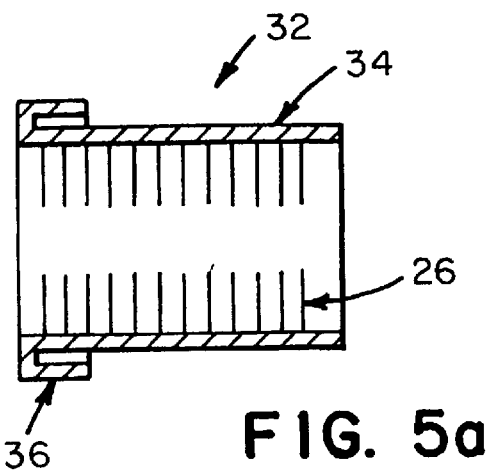
FIG. 5a and 5b shows a side view of an alternative embodiment of the catheter incorporating a brush at its distal end portion in accordance with the present invention.
Figure 5B:
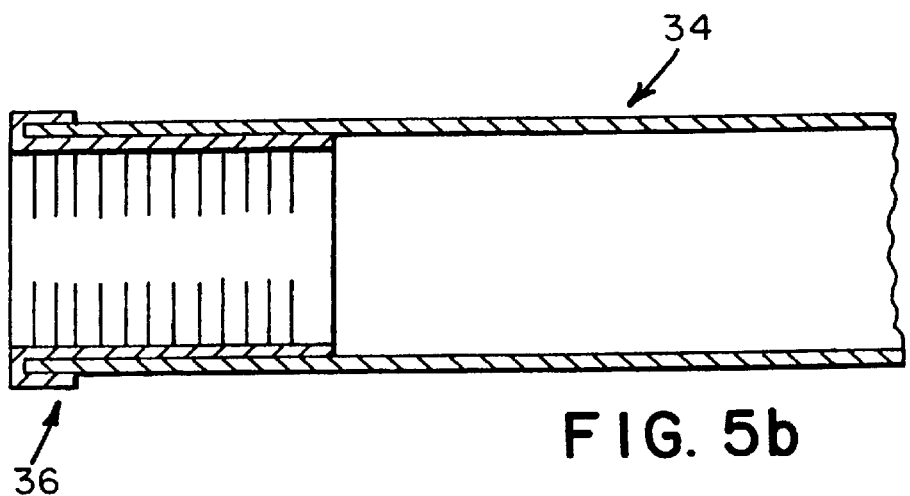

FIGS. 5a and 5b depict an alternative brush assembly. Brush assembly 32 includes a side wall 34 and lip 36. Brush elements 26 may secured to wall 34 by any suitable means. For example, by threading the elements through the wall 34, gluing the elements to the side wall 34, or utilizing a double wall with the ends of the elements 26 through the first wall and secured by the second wall. All suitable securing techniques are considered to be within the scope of the invention. The assembly 32 is then secured over the distal end of the catheter 34 as shown in FIG. 5b. The assembly 32 is preferably glued to the end 36, however, any suitable securing means may be used.

Figure 6:
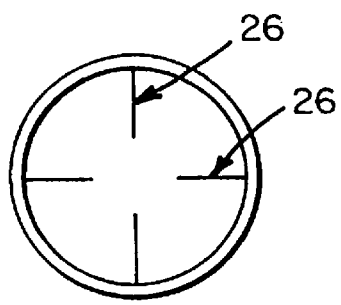
FIG. 6 shows a cross sectional view of a catheter incorporating a brush at its distal end portion in accordance with the present invention.

FIG. 6 shows a cross-sectional view of the brush assembly 22 of the FIG. 3 embodiment and assembly 32 of the FIG. 5a embodiment. Specifically, there is shown 4 upstanding brush elements 26. Of course, any number of elements may be used depending on the type of fiber used in the surgical procedure. The brush elements are preferably manufactured from soft nylon, however, any other suitable material may be used.

Figure 7:
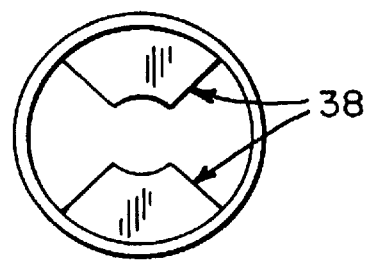
FIG. 7 shows a cross sectional view of an alternative embodiment of a catheter incorporating a removal means at its distal end portion in accordance with the present invention.

Although the preferred embodiment of the means for removing tissue fragments and debris for the distal end portion of the fiber comprises a brush assembly, it is to be understood that any suitable removal means is considered to be within the scope of the invention. For example, FIG. 7 shows an alternative embodiment of the means for removing fragments. Specifically, one or more web elements 38 extend from the wall of the catheter as shown in the figure. The upstanding elements 38 are preferably manufactured from an elastomeric material which serve to wipe the glass 15 of the ADD™ depicted in FIG. 2 or the surface of any fiber encasing used in a particular surgical procedure. However, any other suitable material may be used and is considered to be within the scope of the invention.

SUMMARY OF MAJOR ADVANTAGES OF THE INVENTION

After reading and understanding the foregoing detailed description of an inventive laser therapy system and method of cutting and vaporizing a tissue body in accordance with preferred embodiments of the invention, it will be appreciated that several distinct advantages of the subject laser therapy system and method of cutting and vaporizing a tissue body are obtained.

Without attempting to set forth all of the desirable features of the instant laser therapy system and method of cutting and vaporizing a tissue body, at least some of the major advantages include providing a catheter 20 having a brush assembly 22 secured to a distal end portion 24 of the catheter 20 and a fiber optic 12 which is received in the lumen of the catheter 20. The catheter 20 with inserted fiber optic 12 is directed to a treatment site, such as a bladder and adjacent to the prostate. The fiber optic 12 is extended beyond a distal end 25 of the catheter 20 and a energy is supplied to the fiber using a standard surgical laser system where the body tissue is cut and vaporized by a beam of energy projected from the fiber 14.

The use of the catheter brush assembly 22, 32 of the present invention allows for an effective and efficient technique for cleaning the distal end 19 of a fiber optic. The surgeon is not required to remove the fiber optic from the treatment site during a surgical procedure thereby reducing procedure time and reducing patient trauma. The fiber optic is simply retracted into the catheter lumen through the brush assembly 22, 32 and the distal end of the fiber is wiped free of fragments and debris. Moreover, the surgeon can maintain eye contact with the treatment site throughout the procedure without the need for turning away to wipe the removed fiber. This will insure localized cutting and vaporization without the need for relocating the subject tissue body. Furthermore, a surgeon of any skill can operate the laser therapy system of the present invention to obtain desirable results and can utilize standard laser equipment and viewing equipment.

In describing the invention, reference has been made to a preferred embodiment and illustrative advantages of the invention. Those skilled in the art, however, and familiar with the instant disclosure of the subject invention, may recognize additions, deletions, modifications, substitutions and other changes which fall within the purview of the subject invention.

What is claimed:

1. A method of cutting and vaporizing a tissue body located at a treatment site comprising the steps of:

(a) placing an elongated fiber optic having a distal end portion within the lumen of an elongated catheter such that said fiber is operable between an extended position wherein said distal end portion of said fiber protrudes from said distal end of said catheter and a retracted position wherein said distal end portion of said fiber is received within said catheter lumen, said catheter having at a distal end portion a means for removing tissue fragments and debris from said distal end portion of said fiber comprising at least one removal element operably attached to a distal portion of said catheter and extending a distance into said lumen so as to define a space in cross-section through which said fiber optic travels, said space having a cross-sectional dimension less than a cross-sectional dimension of said fiber optic;

(b) directing said distal end portion of said catheter to a treatment site and placing said distal end of said catheter adjacent the tissue body to be cut and vaporized;

(c) extending said distal end portion of said fiber optic to said extended position and placing said distal end portion of said fiber adjacent to the tissue body to be cut and vaporized;

(d) supplying laser energy through said fiber which directs said energy to said tissue, said energy being of sufficient quantity to cut and/or vaporize said tissue body;

(e) retracting said fiber within said lumen of said catheter such that said distal end portion of said fiber operably engages at least one removal element in order to remove tissue fragment and debris which have become stuck on said distal end portion of said fiber during the cutting and vaporizing of step (d); and (f) repeating steps (c) through (e) as necessary until the tissue body has been sufficiently cut and vaporized.

2. A method of cutting and vaporizing a tissue body located at a treatment site as defined in claim 1 wherein after step (a) and before step (b), said catheter is placed in the receiving channel of a cystoscope.

3. A method of cutting and vaporizing a tissue body located at a treatment site as defined in claim 1 wherein said means for removing tissue fragments and debris from said distal end portion of said fiber optic comprises a plurality of brush elements which occupy the lumen of said catheter at the distal end portion of said catheter.

4. A method of cutting and vaporizing a tissue body located at a treatment site as defined in claim 3 wherein said brush elements radially extend from an inner circumferential surface of said catheter toward said central longitudinal axis of said catheter.

* * * * *